United States Patent [19]
Saleh et al.

[11] Patent Number: 6,126,958
[45] Date of Patent: Oct. 3, 2000

[54] INTRAVAGINAL RINGS WITH INSERTABLE DRUG-CONTAINING CORE

[75] Inventors: Saleh Ismail Saleh, Assuit, Egypt; Harold A. Nash, Harrington Park, N.J.; C. Wayne Bardin, New York, N.Y.; Troy Harmon, Lansdale, Pa.

[73] Assignee: The Population Council, Inc., New York, N.Y.

[21] Appl. No.: 09/316,640

[22] Filed: May 21, 1999

Related U.S. Application Data

[62] Division of application No. 08/850,327, May 2, 1997.
[60] Provisional application No. 60/023,792, Jul. 31, 1996.

[51] Int. Cl.[7] ............................... A61F 6/06; A61F 6/14; A61F 13/00
[52] U.S. Cl. ............................ 424/432; 424/422; 424/430
[58] Field of Search ........................... 424/422, 430, 424/432

[56] References Cited

U.S. PATENT DOCUMENTS

| | | | |
|---|---|---|---|
| 3,545,439 | 12/1970 | Duncan | 128/260 |
| 3,710,795 | 1/1973 | Hiuchi et al. | 128/260 |
| 3,920,805 | 11/1975 | Roseman | 424/15 |
| 3,991,760 | 11/1976 | Drobish et al. | 128/260 |
| 3,995,633 | 12/1976 | Grougeon | 128/260 |
| 3,995,634 | 12/1976 | Drobish | 128/260 |
| 4,012,496 | 3/1977 | Schopflin | 424/15 |
| 4,155,991 | 5/1979 | Schopflin et al. | 424/15 |
| 4,250,611 | 2/1981 | Wong | 29/460 |
| 4,286,857 | 9/1981 | Wong | 128/127 |
| 4,292,965 | 10/1981 | Nash | 128/260 |
| 4,596,576 | 6/1986 | De Nijs | 604/892 |
| 4,822,616 | 4/1989 | Zimmerman et al. | 424/432 |
| 4,888,074 | 12/1989 | Pocknell | 156/217 |

FOREIGN PATENT DOCUMENTS

WO95/00199 of 0000 WIPO.

OTHER PUBLICATIONS

Apter et al., Contraception 42(3):225–295 (1990).
Burton et al., Contraception 17(3):221–230 (1978).
Burton et al., Contraception 19(5):507–516 (1979).
Jackanicz, Contraception 24(4):323–339 (1981).
Sivin et al., Contraception 24(4):341–358 (1981).
Timmer et al., Contraception 42(6) 629–642 (1990).
Toivonen, Contraception 20(5):511–518 (1979).
Akinla et al., Contraception 14(6):671–678 (1976).

*Primary Examiner*—Thurman K. Page
*Assistant Examiner*—Sharon Howard
*Attorney, Agent, or Firm*—Lerner, David, Littenberg, Krumholz & Mentlik, LLP

[57] ABSTRACT

Disclosed is a vaginal ring intended for the release of at least one drug over a prolonged time period. The vaginal ring contains a ring body made of a first polymeric material having at least one hollow internal channel defining an opening to the exterior of said body and which channel is adapted to receive a drug-containing core through said opening, and an intravaginally administerable drug-containing core disposed in the channel. The core is positioned in the vaginal ring body suitably prior to use in order to substantially avoid initial bursts of drug into the tissues of the subject and resultant side effects such as nausea and vomiting. The core contains a pharmaceutically effective amount of at least one intravaginally administerable drug dispersed in a second polymeric material. The first and second polymeric materials may be the same or different. Representative drugs include contraceptive agents and other steroidal substances for use in hormone replacement therapy. Also disclosed are methods for preparing the vaginal rings, kits for assembling the vaginal rings, and methods of using the vaginal rings to achieve intravaginal delivery of drugs to a female.

4 Claims, 11 Drawing Sheets

INTRAVAGINAL RINGS WITH INSERTABLE DRUG-CONTAINING CORE

CROSS REFERENCE TO RELATED APPLICATIONS

This application is a divisional application of application No. 08/850,327 filed May 2, 1997.

The present application claims benefit of U.S. Provisional Application Ser. No. 60/023,792, filed Jul. 31, 1996, the disclosure of which is hereby incorporated by reference herein.

FIELD OF THE INVENTION

The present invention is directed to intravaginal drug delivery devices and methods for the intravaginal administration of drugs, and more particularly, the intravaginal administration of contraceptive agents and agents for hormone replacement therapy.

BACKGROUND OF THE INVENTION

Vaginal rings are torous shaped devices designed to deliver a relatively constant dose of drug to the vagina usually over a period of weeks to months. Typically, they are made of a silicone elastomer and contain a drug released by diffusion though the elastomer. The most common commercial applications have been to deliver low doses of steroids for post-menopausal vaginal conditions. They have also been under development for use in contraception and hormone replacement therapy. Vaginal rings have also been used to administer spermicides, as well as a variety of locally or systematically active medicaments. Vaginal rings have provided several advantages in that their use is controlled by the female; they allow for a better regulated dose of drug without attention by the user; and they avoid the destruction (by the intestine and by first pass through the liver) of an appreciable portion of the daily dosage of some steroids compared to their orally delivered counterparts.

The use of a vaginal ring to deliver drugs requires a ring design that regulates the release rate so as to provide the user with the appropriate daily dose. Among the important factors governing release are the solubility of the drug in the ring elastomer, the surface area of the drug reservoir, the distance the drug must diffuse through the ring body to reach its surface and the molecular weight of the drug. If very high release rates are desired, they can be attained by a drug load at the ring surface as is characteristic of the homogeneous matrix ring design. This design, however, suffers from rapidly declining release rates as the distance the drug must travel to reach the ring surface increases as the drug load near the surface is depleted. If moderately high release rates are needed to provide the appropriate dose, a design which modulates release rate by imposing a layer of drug-free elastomer between the drug reservoir and the ring exterior is appropriate. This may be attained by coating a homogeneous ring, or to conserve drug, by incorporating a drug-free core, a shell design may be used. If an even lower release rate is desired, the drug may be confined to a small diameter at the center of the ring ("core ring"). Finally, the drug-loaded core may not encircle the ring but instead be of short length. Numerous types of vaginal rings have been described in the patent and non-patent literature alike. See, e.g., U.S. Pat. Nos. 4,012,496 and 4,155,991 (both to Schopflin et al.), U.S. Pat. No. 4,292,965 (Nash), U.S. Pat. No. 3,545,439 (Duncan), U.S. Pat. No. 3,920,805 (Roseman), U.S. Pat. Nos. 3,991,760 and 3,995,634 (both to Drobish et al.), U.S. Pat. No. 3,995,633 (Gougen), U.S. Pat. Nos. 4,250,611 and 4,286,587 (both to Wong), U.S. Pat. No. 4,596,576 (de Nijs); W095/00199 (Lehtinen et al.), NL 8500-470-A; and Apter et al., Contraception 42: 285–295 (1990), Burton et al., Contraception 12: 221–230 (1978), Burton et al., Contraception 19: 507–516 (1979), Jackanicz, Contraception 24: 323–339 (1981), Sivin et al., Contraception 24: 341–358 (1981), Timmer et al., Contraception 43: 629–642 (1990), and Toivonen, Contraception 20: 511–518 (1979).

Vaginal rings have been used experimentally to deliver the contraceptive agent, ethynylestradiol. However, an undesirable percentage of women who have used vaginal rings for this purpose had complained of nausea and vomiting, particularly from the first cycle of use of the rings due to an initial burst of steroid release. The manufacture of the so-called "core" rings presents additional problems. One problem is the physical one of placing the cores in the ring body by techniques adapted to facile manufacture. Another is that drugs with reactive groups such as ethynyl, amino groups, or sulfhydryl groups may prevent vulcanization of preferred silicone polymers. One method of introducing short lengths of drug-loaded cores is to mold a half ring with a center groove, place the core in the groove, change molds and inject the second half of the ring. This technique, while feasible, requires two molding steps for manufacture of the ring body. It also limits elastomer choice when dealing with reactive drugs such as ethynylestradiol.

Hence, a need remains for a vaginal ring that does not cause nausea and vomiting, and other problems associated with some devices, while still providing the other advantages that vaginal rings have offered.

SUMMARY OF THE INVENTION

One aspect of the present invention is directed to a vaginal ring which contains a vaginal ring body of a first polymeric material having at least one hollow internal channel defining an opening to the exterior of said body and which channel is adapted to receive a core containing an intravaginally administerable drug through the opening, and a core positioned in the channel, wherein the core contains a pharmaceutically effective amount of at least one intravaginally administerable drug dispersed in the second polymeric material. The first and second polymeric materials may be the same or different.

In preferred embodiments, the first and/or second polymeric material is a silicone elastomer such as polydimethylsiloxane or a copolymer of dimethylsiloxane and methylvinylsiloxane, or a polyurethane. The vaginal ring body may also contain a particulate filler material and/or a pharmaceutically effective amount of a vaginally administerable drug, which may be the same or different from the drug contained in the core. Preferred drugs include contraceptive agents such as progestational compounds (e.g., norethindrone acetate and NESTORONE™ (i.e., 16-methylene-17α-acetoxy-19-norpregnene-3,20-dione)), and estrogenic substances (e.g., ethynylestradiol) and other steroidal compounds useful in hormone replacement regimens. In a more preferred embodiment, the core contains two drugs, more preferably two contraceptive agents, e.g., the first being the NESTORONE™ progestin or norethindrone acetate, and the second being ethynylestradiol. In another preferred embodiment, the vaginal ring body contains estradiol, and the core contains a progestin such as the NESTORONE™ progestin, and is used in hormone replacement therapy. In yet other preferred embodiments, the vaginal ring contains a plurality (e.g., two or three) of drug-containing cores, wherein each core may contain the same or a different drug, or more than one drug.

In other preferred embodiments, the drug is present in the core in an amount of from about 1% to about 65% of the weight of the core. The vaginal ring has an overall diameter of from about 4 mm to about 10 mm. The core has a cross-sectional diameter of from about 1.5 mm to about 5 mm, and a length of from about 5 mm to about 40 mm, and is positioned in the vaginal ring body such that the cross-sectional diameter of the ring body exceeds the cross-sectional diameter of the core by an average of 1 mm in all directions. The hollow channel of the vaginal ring may also contain a sealant such as a silicone medical grade adhesive (e.g., a polymethylsiloxane having methyldiacetoxysilyl end groups) for securing the core in the hollow channel of the ring body and/or separating the core from the exterior environment so as to prevent passage or diffusion of the drug to the exterior environment directly from the core.

Another aspect of the present invention is directed to a method of intravaginally administering a drug to a female over a predetermined time period, which involves the steps of:

(a) providing a vaginal ring body containing a first polymeric material having at least one hollow internal channel defining an opening to the exterior of said body and which channel is adapted to receive a intravaginally administerable drug-containing core through the opening;

(b) providing a core containing a pharmaceutically effective amount of the intravaginally administerable drug dispersed in a second polymeric material, wherein the first and second polymeric materials may be the same or different;

(c) positioning the core in the channel to thereby assemble the vaginal ring; and (d) inserting the vaginal ring into the vagina so that the drug will be intravaginally delivered to the female for the predetermined period of time. In preferred embodiments, the vaginal ring is assembled (e.g., the core is positioned in the channel) within about four days prior to use, more preferably within about 24 hours prior to use, and most preferably substantially immediately prior to use, such that upon administration, there is no (i.e., negligible) initial burst of drug that otherwise tends to cause undesirable side effects such as nausea or vomiting. In addition, the vaginal ring body may be provided by molding the first polymeric material having the at least one hollow internal channel in a single step.

Yet another aspect of the present invention is directed to a kit which contains a suitably shaped vaginal ring body comprising a first polymeric material having at least one hollow internal channel defining an opening to the exterior of said body and which channel is adapted to receive an intravaginally administerable drug-containing core through the opening, and at least one core to be positioned in the channel, wherein the core contains a pharmaceutically effective amount of an intravaginally administerable drug dispersed in a second polymeric material, wherein the first and second polymeric materials may be the same or different. In preferred embodiments, the kit also contains a sealant for sealing the hollow channel after positioning the drug-containing core therein, and/or applicators for positioning the core in the channel and applying the sealant to the channel. The sealant is preferably a medical grade adhesive such as a polymethylsiloxane having methyldiacetoxysilyl end groups. The applicator is preferably a syringe.

The vaginal rings and the methods of the present invention offer several additional advantages over prior art drug delivery mechanisms. They provide for a substantially constant release of drug as compared to oral or injectable modes of drug administration, and they maintain the potency of drugs that are susceptible to destruction as they pass from the intestine through the liver immediately after absorption from the gut.

A further aspect of the present invention is directed to a method for the preparation of a vaginal ring by a relatively simple procedure in which the first polymeric material is molded in a single step to form the vaginal ring body with at least one hollow internal channel, followed by vulcanizing the vaginal ring body and inserting the drug-containing core in the hollow internal channel, thereby assembling the vaginal ring. In a preferred embodiment, the first polymeric material is an elastomeric material which is molded with at least one removable rod or other suitable device to produce a continuous, annular ring body with a corresponding predetermined number of channels. In preferred embodiments, the molding step is conducted in the presence of a catalyst. The core is prepared by mixing the drug with an elastomeric material, followed by molding and then vulcanizing. In another preferred embodiment, the core may be vulcanized in situ in the ring body, depending upon whether the drug is one in which the initial burst is to be avoided. For example, in cases where initial drug bursts are to be avoided, the ring body and core are vulcanized separately, and the cores are introduced into the channels suitably prior to use. In embodiments where an initial drug burst is not a problem, the core may be vulcanized in situ in the ring body subsequent to its introduction into the channel. In these embodiments, the drug-containing core may be effectively introduced by injecting a mixture of the drug, the second polymeric material and a suitable catalyst into the hollow internal channel of the vaginal ring body so that the drug-containing core is formed in situ.

In preferred embodiments, the diameter of the core relative to the channel may vary slightly; it may be substantially equal to or slightly greater or smaller than the channel diameter. In preferred embodiments, the core diameter is substantially equal to or even slightly greater than that of the channel, such that following insertion or formation of the core into the channel, surface contact is maintained between the outer longitudinal surfaces of the core and the surface of the channel. The method is less time consuming and more easily mechanized than current methods. Therefore, the core may be inserted into the ring body during the manufacturing process, or packaged separately and inserted suitably prior to use, in accordance with other aspects of the present invention.

DETAILED DESCRIPTION OF THE PREFERRED EMBODIMENTS

Figure 1A:
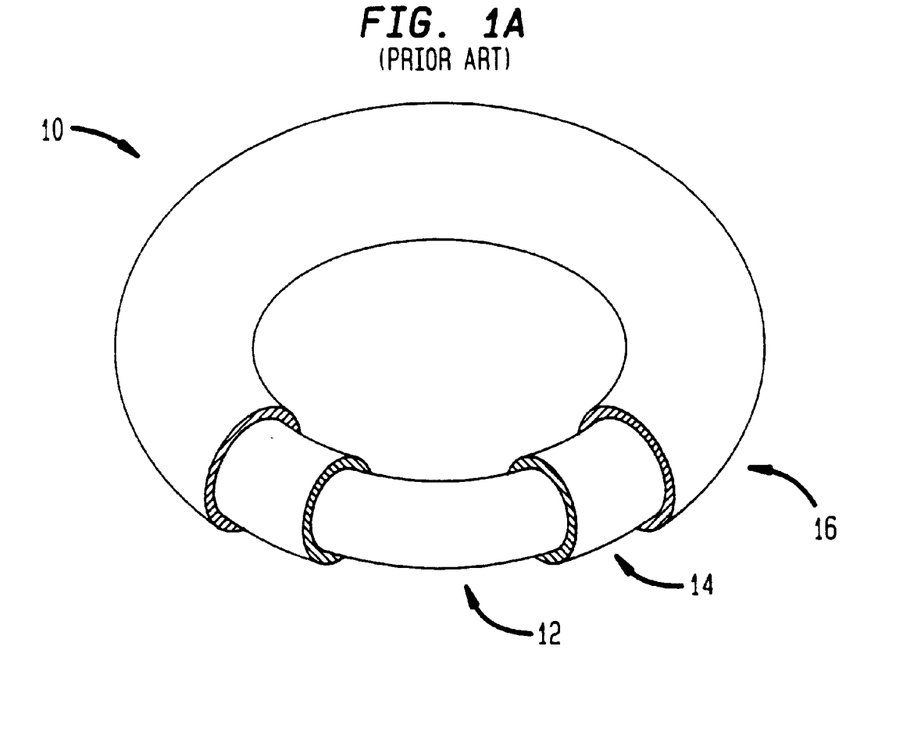
FIG. 1A is a cutaway view of a prior art "shell" vaginal ring.
Figure 1B:
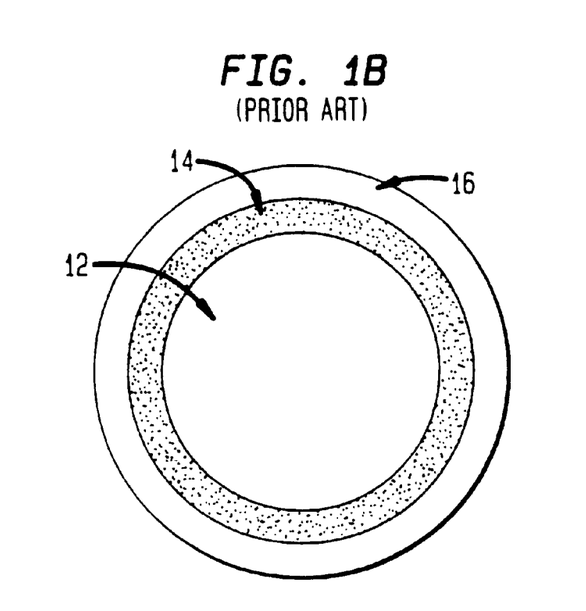
FIG. 1B is a cross-sectional view of a prior art vaginal ring of "shell" design.
Figure 2A:
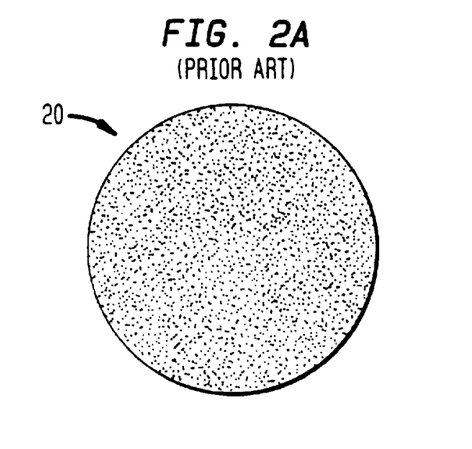
FIG. 2A is a cross-sectional view of a prior art "homogenous" vaginal ring.
Figure 2B:
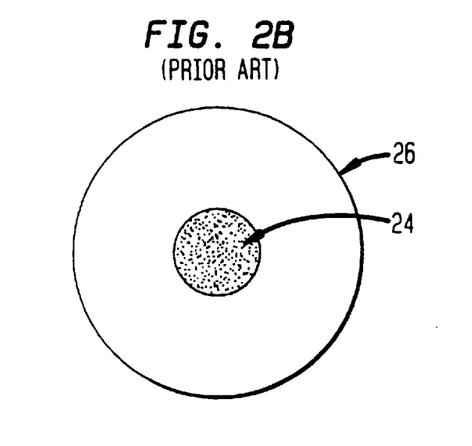
FIG. 2B is a cross-sectional view of a prior art vaginal "core" ring.

Representative prior art vaginal rings are illustrated in FIGS. 1A, 1B, 2A, 2B, and 3. Shell ring 10, illustrated in FIGS. 1A and 1B, contains inert core 12 surrounded by drug (e.g., steroid)-containing layer 14, which in turn is surrounded by drug release-controlling layer 16. Thus, the steroid load is in a zone beneath the ring surface but not extending to the center of the ring. Shell rings were developed to deliver a lesser dose than that which would be initially delivered by homogenous ring 20, illustrated in FIG. 2A. In the homogenous ring, the drug is substantially uniformly dispersed throughout the volume of the vaginal ring. If even lower doses are desired, the drug or steroid load may be delivered via a so-called core ring, as illustrated in FIG. 2B. The drug load is contained totally in core 24 of ring 26.

Figure 3:
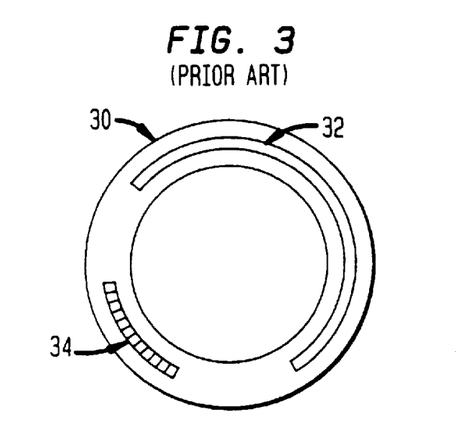
FIG. 3 is a cross-sectional view of a prior art modified "core" ring.

A modification of the core ring is illustrated in FIG. 3. Vaginal core ring 30, having a total diameter of 58 mm, and a cross-sectional diameter of 7.6 mm, contains a first, non-extensive core 32 containing the progestational compound, norethinderone acetate, and a second, non-extensive core 34 which contains the estrogenic compound, ethynylestradiol. Each of cores 32 and 34 has a cross-sectional diameter of 2 mm. Applicants have unexpectedly found that the nausea and vomiting that has typically occurred in some women shortly after beginning use of a vaginal ring with an ethynylestradiol-containing core 30 is due to the initial burst of drug from the ring caused by the accumulation of the drug in the ring body between the core and the outer surface of the ring during post-manufacture storage. These experimental results are described in detail in Example 1. The vaginal rings of the present invention, on the other hand, eliminate or substantially alleviate undesirable side effects such as nausea and vomiting often associated with the use of vaginal drug delivery systems containing estrogens.

Figure 4A:
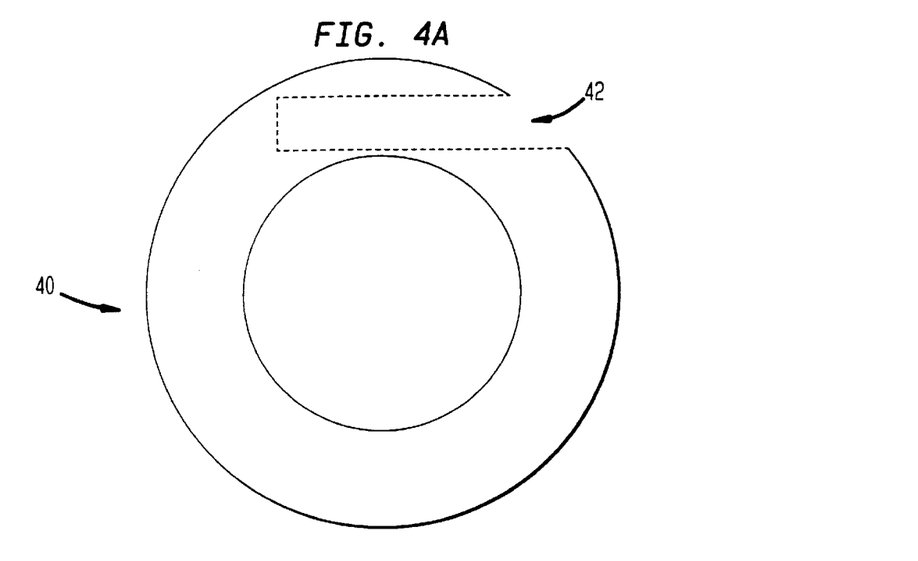
FIG. 4A is a schematic view of a vaginal ring body according to the present invention.
Figure 4B:
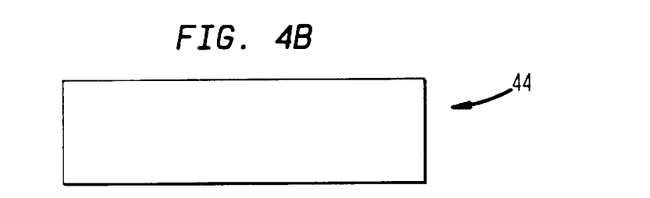
FIG. 4B is a schematic view of a drug-containing core according to the present invention.
Figure 4C:
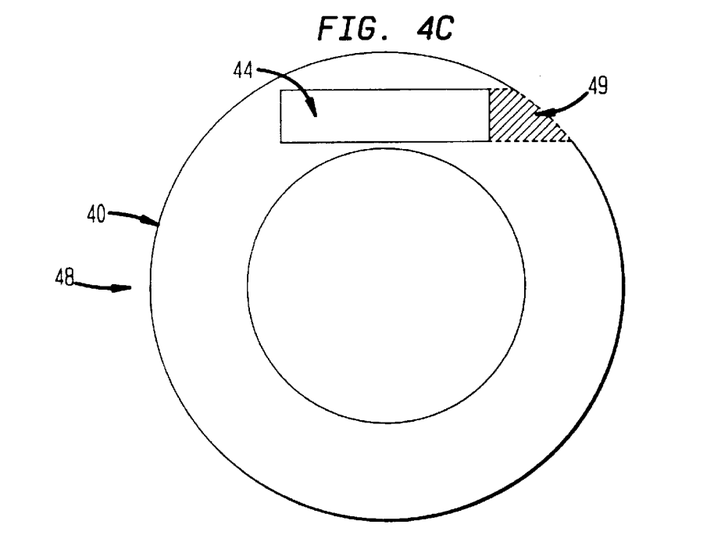
FIG. 4C is a schematic view of an assembled vaginal ring according to the present invention.

FIGS. 4A, 4B, and 4C illustrate a preferred embodiment of the present invention. Turning to FIG. 4A, vaginal ring body 40, is shaped in the form of a continuous, annular ring, and is composed of a first polymeric material containing at least one hollow internal channel 42 which opens or is opened to the exterior environment and which is adapted to receive at least one drug-containing core 44 (FIG. 4B) through the opening. As illustrated in FIG. 4A, the hollow channel is in communication with the exterior of the ring body through an opening in the ring body. By the term "ring", it is meant any continuous curved or torous shape that does not compromise ease of administration (insertion), comfort, esthetic appeal, or efficacy. By the term "internal", it is meant that there is no portion of the core which is exposed to or in contact with the outer surface of the ring body once the vaginal ring is fully assembled (and the opening is sealed), such that when administered, the drug will diffuse from the core directly into the tissue of the subject.

In preferred embodiments, the core is inserted into the channel suitably prior to use (i.e., administration or insertion of the vaginal ring by the patient). By the phrase "suitably prior to use," it is meant that the drug-containing core is positioned in the hollow channel at a time such that accumulation of the drug in ring body 40 (i.e., in the body of the ring between the core and the outer surface) and the resultant initial burst of the drug upon subdermal administration, are negligible (i.e., side effects such as nausea and vomiting that occur with some steroids are minimized). In preferred embodiments, the core is positioned in the channel no later than about 4 days prior to use, more preferably within about 24 hours prior to use, and most preferably substantially immediately prior to use. In some unusual situations, however, core insertion may be conducted even more than one week prior to administration of the vaginal ring of the present invention. For example, vaginal rings fully assembled at least ten days prior to use, and which are stored at temperatures substantially below room temperature, e.g., about 5° C., will not cause an initial burst or the attendant side effects. The vaginal ring may also contain a pharmaceutically effective amount of at least one vaginally administerable drug, preferably uniformly dispersed in the first polymeric material.

Core 44, illustrated in FIG. 4B, contains a pharmaceutically effective amount of an intravaginally administerable drug dispersed, preferably in the form of a substantially uniform dispersion, in a second polymeric material. The first and second polymeric materials may be the same or different. FIG. 4C illustrates an assembled vaginal ring 48 wherein core 44 is disposed or positioned in hollow channel 42, and secured in the channel by a sealant, which in a preferred embodiment is silicone medical grade adhesive 49.

Suitable first and second polymeric materials for use in the present invention are compatible with each other and the drug (e.g. the polymer cannot inactivate the drug); they are nontoxic and nonabsorbable in the subject; they are capable of being suitably shaped for intravaginal administration; and they allow for the controlled diffusion of the drug from the core, through the ring body and into the tissues of the subject. Examples include elastomers such as polysiloxanes, polyurethanes, ethylene/vinyl acetate copolymers, and copolymers of dimethylsiloxanes and methylvinylsiloxanes. Preferred polymeric materials are silicone elastomers, particularly polydimethylsiloxanes and derivatives (e.g., containing fluoro- or phenyl- groups) thereof. The structural integrity of the ring body may be enhanced by the addition of a particulate material such as fumed silica or diatomaceous earth.

The sealant closes the channel after core placement and may also be used to form a firm bond between the ring body and the core, and to serve as a lubricant during core insertions. It also minimizes diffusion of the drug through the axial ends of the core. Preferred sealants include medical grade adhesives such as polydimethylsiloxanes, and particularly those having methyl diacetoxysilyl end groups which vulcanize upon exposure to moisturized air.

The intravaginally administered drug(s) contained in the core(s) and optionally the vaginal ring include any physiologically or pharmacologically active substance that because of its potency and solubility in the ring elastomer, can be released in adequate doses from ring bodies with central drug-bearing cores, particularly cores of less that 60 mm cumulative length. Among drugs meeting these criteria, those used chronically and those with a low acceptable dose range are particularly apt candidates. Examples include contraceptive steroids, and certain steroids for hormone replasteroidsherapy. Representative steroids include progesterone, NESTORONE™ (i.e., 16-methylene-17α-acetoxy-19-norpregnene-3,20-dione), NESTORONE™ acetate, norethindrone acetate, 3-ketodesogestrel, desogestrel, lynestrenol, norgestrienone, nomegestrol acetate, medroxyprogesterone acetate, gestodene, ethynodiol diacetate, norethindrone, ethynylestradiol, mestranol, estradiol benzoate, estradiol cypionate, estrone and estradiol valerate.

By the term "pharmaceutically effective," it is meant an amount which is sufficient to effect the desired physiological or pharmacological change in the subject. This amount will vary depending upon such factors as the potency of the particular drug, the desired physiological or pharmacological effect, and the time span of the intended treatment. Those skilled in the pharmaceutical arts will be able to determine such amount for any given drug in accordance with standard procedures. See, e.g., Chien et al., J. Pharm. Sci. 63, 365 (1974), and U.S. Pat. No. 3,710,795. In a preferred embodiment wherein the drug is a contraceptive agent, the "pharmaceutically effective" amount is an amount sufficient to result in contraception for a predetermined time period, which is generally from about 3 months to about 1 year. In general, this amount is in the range from about 5.0 µg to about 200 µg/day. The amount of the drug in the core will generally be in a range of from about 2–65% by weight of the core, depending upon the daily dose and the duration of treatment desired. Greater amounts of drug can be advantageously achieved by omitting particulate filler materials in the core polymeric material. In another preferred embodiment, the vaginal ring is used in hormone replacement therapy and the vaginal ring body contains estradiol or estrone, and the core contains a progestin such as NESTORON™.

Figure 5:
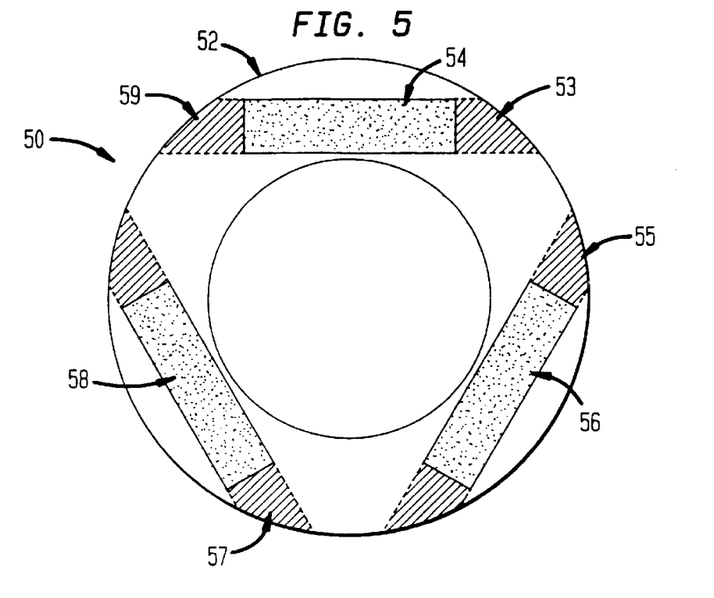
FIG. 5 is a schematic view of another assembled ring according to the present invention.

The ring body may contain a plurality of drug-containing cores. FIG. 5 illustrates another preferred embodiment of the present invention, wherein intravaginal ring 50 contains ring body 52 having cores 54, 56 and 58 disposed in hollow channels 53, 55 and 57, respectively, which are sealed therein with medical grade silicone adhesive 59. The drug contained in each of cores 54, 56 and 58 may be the same or different. In addition, one or two of the cores may contain a drug, an initial burst of which would not cause undesirable side effects in a patient, so that the core(s) containing such drug may be inserted (such as by injection) into the ring body after molding of the ring body and prior to packaging and storage.

The vaginal ring bodies of the present invention are prepared using a single molding step. In one preferred embodiment, the first polymeric material is cast in a mold having removable, rod-like inserts extending therein, which when removed, form channels into which the drug-containing core will be inserted. The thus-molded ring body is then vulcanized in accordance with standard techniques. Vulcanization can be conducted at room temperature or at elevated temperatures, and, if necessary, in the presence of a suitable catalyst such as heavy metals (e.g., platinum), peroxides (e.g., 2,4-dichlorobenzoyl peroxide), stannous octoate and dibutyltin. The drug-containing core is also prepared in accordance with standard techniques such as extrusion and injection molding. In a preferred embodiment, the drug is mixed with the second polymeric material, and the mixture is injected into a suitably shaped mold, and then vulcanized. The vulcanization catalyst is selected so as to be effective in the presence of the drug and not to interact chemically with drug. Vulcanization of the ring bodies and the core may optionally be followed by a post-curing step.

In another preferred embodiment, vulcanization of the cores is performed after the introduction of the drug into the hollow channel of the ring body. This embodiment is employed when an initial burst of the drug does not cause undesirable side effects. In those instances when an initial burst of a drug will not cause unacceptable side effects, the ring body hollow channel itself can serve as the mold—it "receives" the drug-containing core by allowing for the injection of a mixture of the drug, second polymeric material and a catalyst which then forms a core in situ. The core is then vulcanized.

The disclosed methods for preparing the vaginal rings of the present invention offer several advantages in addition to avoiding burst effects. They allow for the production of the ring body in a single step. Core placement is facilitated because it is simply pushed into a longitudinal channel, or in alternative embodiments, it is allowed to form in situ. In addition, the method is less time consuming and more easily mechanized, of course, these advantages are realized even when the cores are inserted immediately after molding of the ring body, prior to packaging and/or storage. Further, in those embodiments where curing of the ring body is conducted in the absence of drug, interference with vulcanization due to the presence of drug, which has in the prior art precluded some drug/polymer combinations, is avoided. In addition, the absence of drug during ring body manufacture allows for the use of higher temperatures and shorter molding times.

In a more preferred embodiment, the ring body and the drug-containing core are suitably packaged together so that the device can be assembled by a physician, pharmacist, or even the subject, suitably prior to use. In preferred embodiments, the vaginal ring is assembled no later than about four days prior to administration, in a more preferred embodiment, within about 24 hours prior to use, and in a most preferred embodiment, substantially immediately prior to use. The kits preferably contain a sealant for securing the drug-containing core in the hollow channel of the ring body. Preferred sealants are medical grade adhesives as disclosed above. The kit may further contain an applicator, such as a syringe, for delivering or inserting the sealant into the hollow channel. In a preferred embodiment of assembling the device, a small aperture is made in the support at the closed end of the hollow channel, to allow for the escape of air when the core is introduced. The channel is then approximately half-filled with the sealant, followed by insertion of the core, which assures a firm, uniform contact between the drug-containing core and the inner surface of the hollow channel. Additional sealant is added and the excess, which is also squeezed from the open end of the channel, is removed while sealing the open end of the channel flush with the outer surface of the support.

In a more preferred embodiment, an even simpler procedure is used to assemble the vaginal ring. The parameters that define the optimal difference between the core and channel diameters are: (1) anticipation of the amount of shrinkage of core diameter that will occur as drug is lost from the core during use; (2) ease of insertion of the core; (3) avoidance of distortion of the vaginal ring to the point of compromising aesthetic appeal; and (4) compromise of drug release due to loss of contact between core and ring body. Accordingly, in this embodiment, the diameter of the core is substantially equal to, or even slightly greater than that of the channel so that contact between the core and ring body is maintained due to the elasticity of the ring body. Unlike the embodiment above, there is no need to apply adhesive to the channel prior to insertion of the core. Rather, a suitable medical grade adhesive is applied after insertion of the core to seal the channel. The core may be inserted into the channel with a suitable applicator, such as a thin-walled trocar.

The vaginal rings of the present invention have an overall diameter of from about 48 to about 60 mm, and a cross-sectional diameter of from about 4 to about 10 mm, which dimensions depend in part on the dimensions of the core. Preferably, the relevant dimensions of the ring and the core are established such that upon assembly of the device, the cross-sectional diameter of the support exceeds the cross-sectional diameter of the core by an average of at least 1 mm in all directions. The dimensions of the core are determined on the basis of factors such as the amount of drug to be delivered to the subject, the time over which the drug is to be delivered, the diffusion characteristics of the drug, and by the relative ease with which complimentary-sized channels can be formed in the support. In general, the core has a length of from about 5 mm to about 40 mm. For example, to accommodate a core having a length of about 26 mm, it is preferred that the ring body have a diameter of about 60 mm, and a cross-sectional diameter of about 9 mm. To accommodate a core having a length of about 40 mm, the corresponding hollow channel may -be slightly curved. The drug-containing core has a diameter of from about 1.5 to about 5 mm, and will vary relative to the diameter of the hollow channel of the ring body depending upon the method in which the vaginal ring is to be assembled. The present inventors have found that core diameters of about 3 mm are particularly well suited for delivery of drug for about one year, and thus offer the additional advantage of decreasing the cost per cycle of using the vaginal ring. In the embodiment above wherein a sealant is introduced into the hollow channel both before and after insertion of the core, the diameter of the core is typically less than that of the channel, e.g., a channel diameter of 3.18 mm will easily accommodate a 3 mm core. In the more preferred embodiment, the core diameter slightly exceeds that of the channel, e.g., a 2.8 mm channel will accommodate a 3.0 mm core. In general, core diameter may vary by plus or minus 10% of the channel diameter.

The invention will be further described by reference to the following detailed examples. These examples are merely illustrative, and not limitative of Applicants' invention in any way. Unless otherwise indicated, all percentages are by weight, and storage temperature of the vaginal rings after assembly and prior to measurement of release rates was at ambient temperature.

EXAMPLE 1

Illustration of the burst effect and the effects of storage conditions thereon.

Vaginal rings illustrated in FIG. 3 but containing only a single core were prepared using room temperature vulcanizable polydimethylsiloxane. Stannous octoate (stannous 2-ethylhexanoate) was used as catalyst to effect curing. The dimensions of the ring body were 56 mm overall diameter and 9 mm cross-section diameter. The core was made of the same polymer mixed with ethynylestradiol to give a concentration of 7% steroid in the core. Core dimensions were 2.2×20 mm.

The ring body was made in two steps with the core being centered in the first half ring, which was then overlaid with polydimethylsiloxane to complete the ring body. In vitro measurements of release rate were made after storage as indicated in Table 1, and graphically illustrated in FIG. 6. Measurements were made on four rings at each time and temperature combination.

TABLE 1

In vitro release of ethynylestradiol at periods of storage after ring manufacture

| | | $\mu$g EE/day ± SD (N = 4) Day | | |
|---|---|---|---|---|
| Time Storage | Temp. | 1 | 2 | 3 |
| 1 day | Room | 26 ± 2 | | |
| 2 wks | 5° | 45 ± 5 | 22 ± 6 | 20 ± 7 |
| 2 wks | Room | 60 ± 6 | 23 ± 4 | 17 ± 3 |
| 2 wks | 37° C. | 116 ± 7 | 24 ± 6 | 20 ± 3 |
| 2 mo | 5° | 56 ± 3 | 33 ± 2 | 28 ± 4 |
| 2 mo | Room | 74 ± 3 | 24 ± 2 | 21 ± 5 |
| 2 mo | 37° | 136 ± 19 | 33 ± 4 | 19 ± 2 |
| 6 mo | 5° | 50 ± 10 | 30 ± 6 | 24 ± 6 |
| 6 mo | Room | 126 ± 6 | 39 ± 6 | 27 ± 6 |
| 6 mo | 37° | 135 ± 5 | 35 ± 5 | 20 ± 1 |

Figure 6:
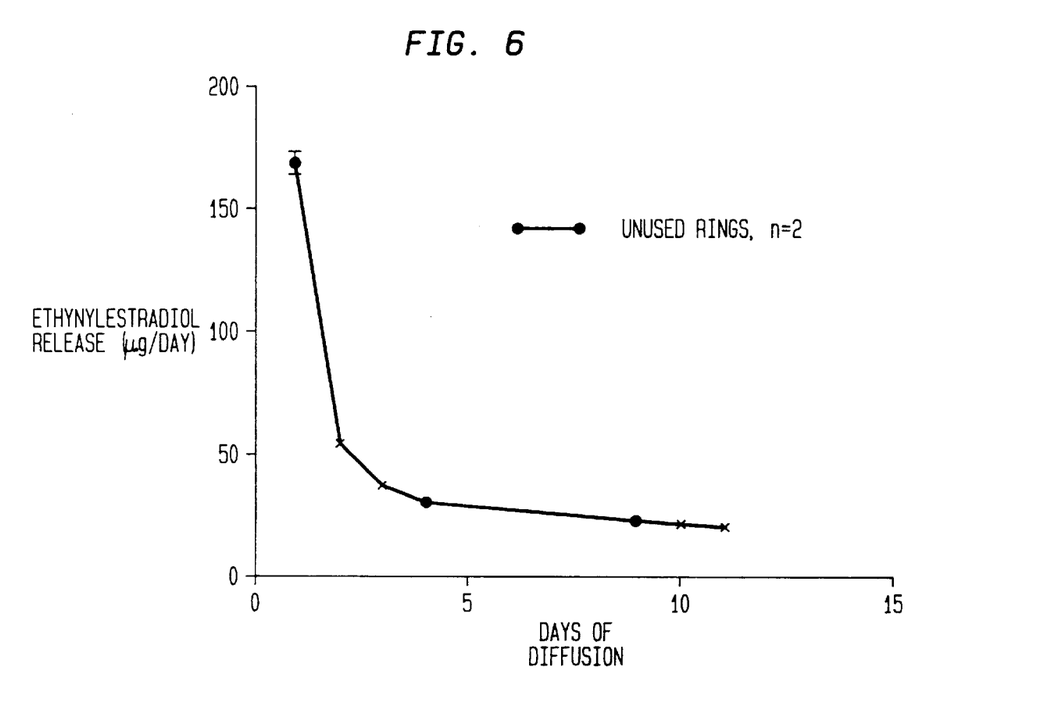
FIG. 6 graphically illustrates the in vitro release of ethynylestradiol from vaginal rings illustrated in FIG. 3.

The release results indicate that the magnitude of first day burst increases with storage time, with even greater and more rapid increases exhibited at higher storage temperatures. As illustrated in FIG. 6, the burst is largely confined to the first day following insertion of the vaginal ring.

EXAMPLE 2

Illustration of use of the intravaginal drug delivery devices of the present invention to avoid a burst of steroid release.

Vaginal rings of the present invention were prepared with two channels. The ring body was of 56 mm overall diameter and 8.4 mm cross-sectional diameter. The elastomer used in molding the rings was a platinum catalyzed dimethylsiloxane/methylvinylsiloxane copolymer manufactured by Applied Silicone Corp. of Ventura, Calif. The elastomer is identified as LSR 25-10:1. It is packaged in two parts which are mixed together in the ratio 10:1 to effect vulcanization.

Figure 7:
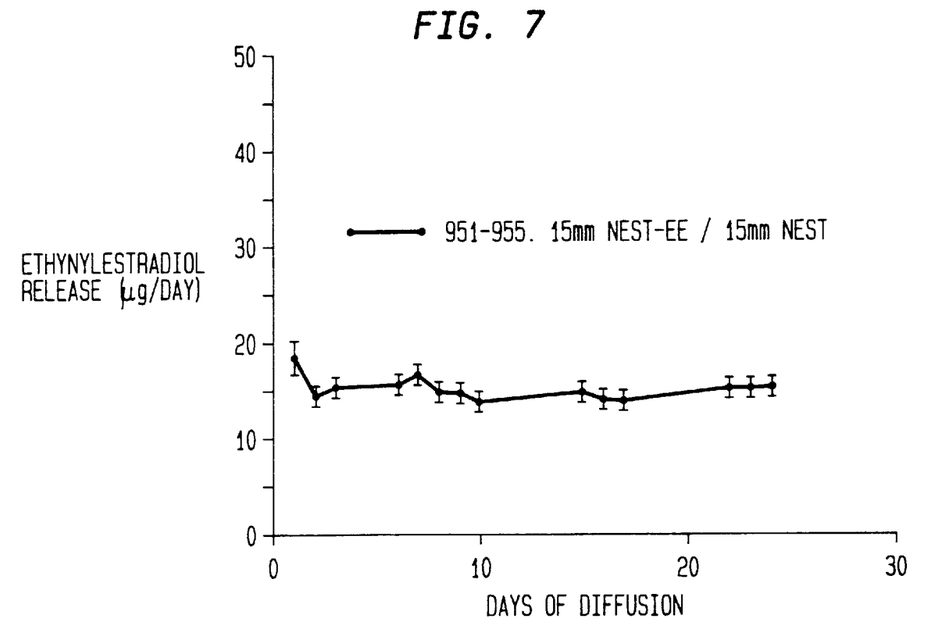
FIG. 7 graphically illustrates the in vitro release of ethynylestradiol from vaginal rings of the present invention.
Figure 8:
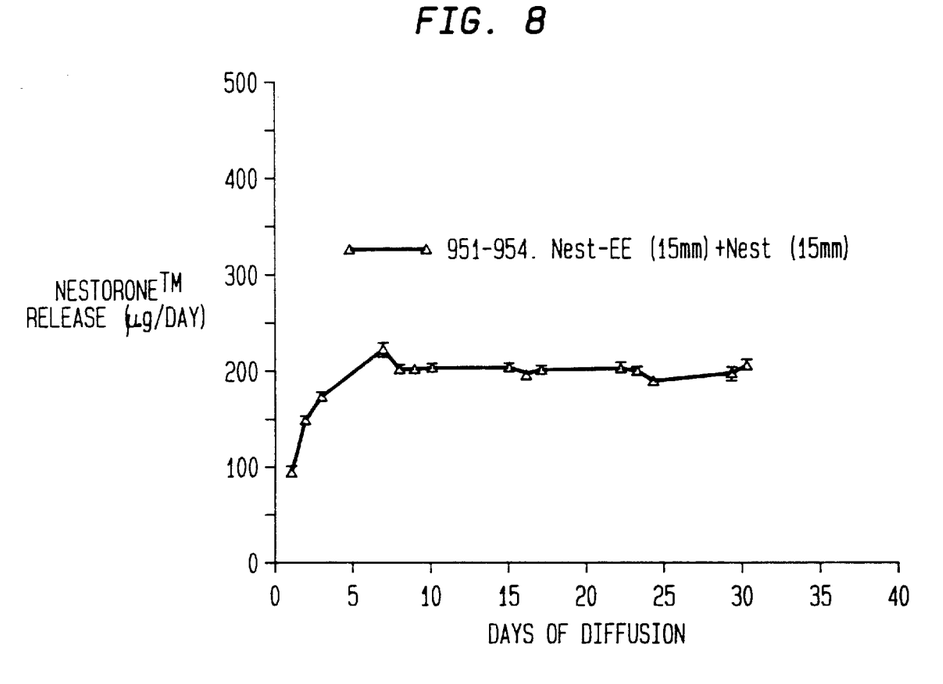
FIG. 8 graphically illustrates the release of NESTORONE™ progestin from vaginal rings of the present invention.

The mixture was injected into a mold with a removable steel rod to produce channels for core insertion. Curing was conducted at 105° C. for 30 min. Cores were prepared by mixing steroid with a room temperature-vulcanizable polydimethylsiloxane (MED 6382, obtained from NuSil Silicone Technology of Carpinteria, Calif.) Two cores were prepared and inserted into each ring. Each was 3×15 mm. One contained 50% NESTORONE™ and one contained 40% NESTORONE™ and 12% ethynylestradiol. The channels in the ring body were partially filled with polydimethylsiloxane medical adhesive and the cores were inserted 17 hrs before beginning in vitro release measurements. The release patterns are shown in FIGS. 7 and 8. They show only negligible burst of ethynylestradiol release, and no burst of NESTORONE™ release.

EXAMPLE 3

Illustration of the use of the present invention to avoid a burst of steroid release.

Figure 9:
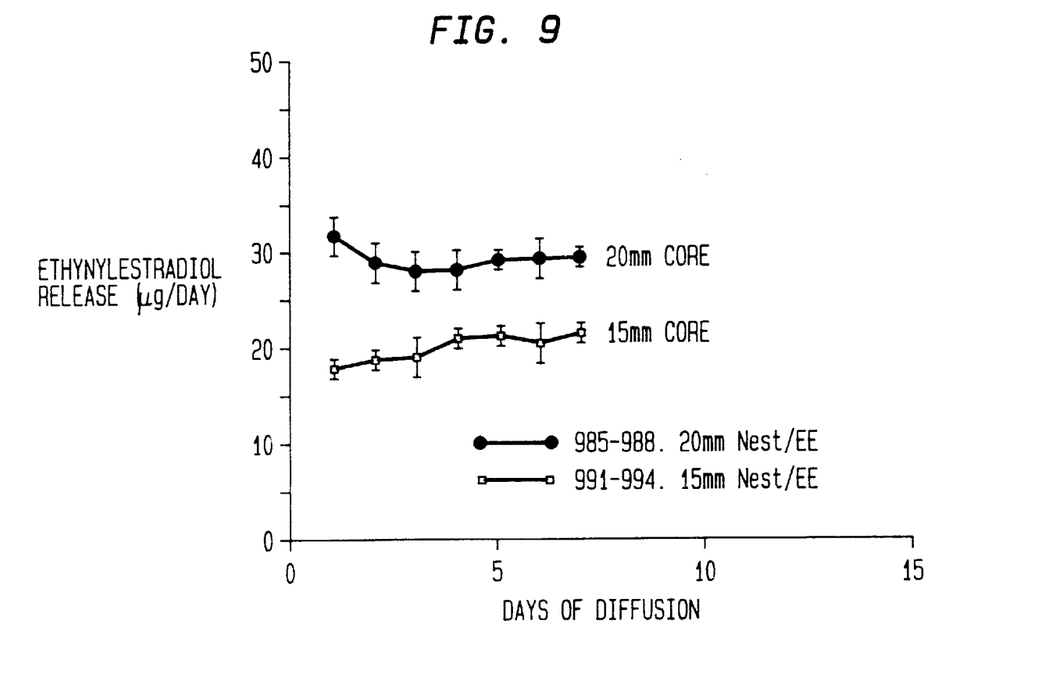
FIGS. 9 and 10 graphically illustrate the release of ethynylestradiol and NESTORONE™, respectively, from different vaginal rings of the present invention, which were assembled 17 hours prior to in vitro release measurement.
Figure 10:
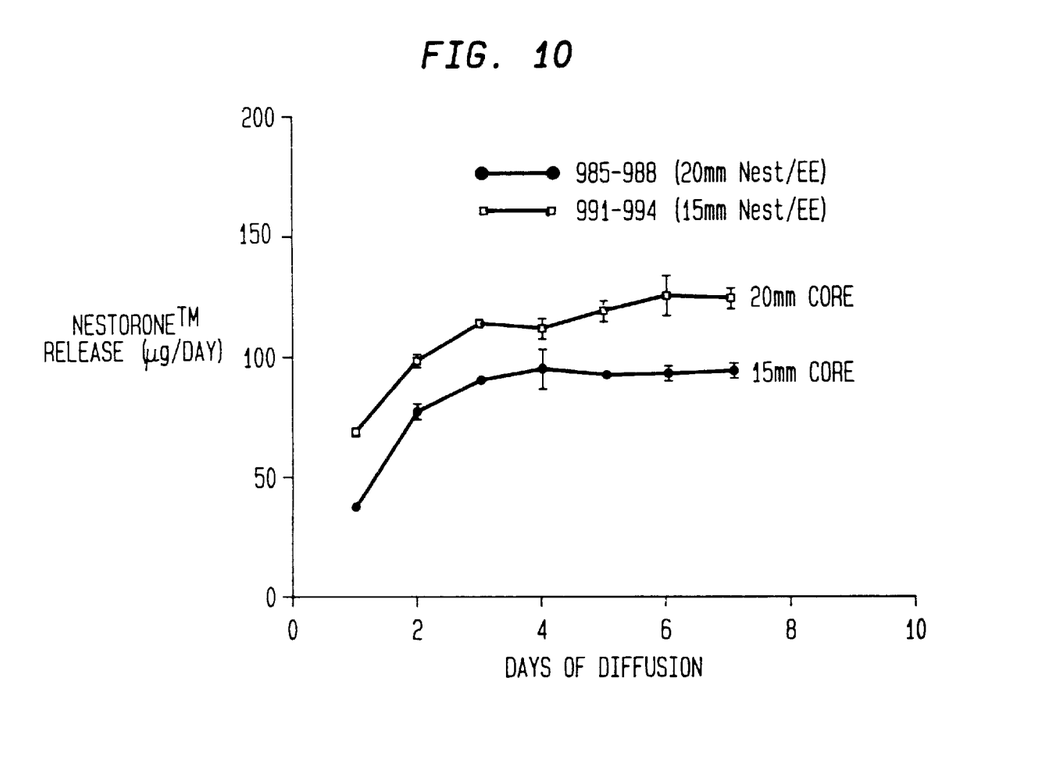

Vaginal rings of the present invention were prepared using a platinum catalyzed dimethylsiloxane/methylvinylsiloxane copolymer manufactured by Applied Silicone Corp. of Ventura Calif., identified as LSR 25-10:1. The ring bodies had a 56 mm overall diameter and 8.4 mm cross-sectional diameter. The two parts of the elastomer composition were mixed together in a 10:1 ratio, and injected into a mold with a removable steel rod to produce a channel for core insertion. Cure was effected by heating 30 minutes at 105° C. The cores were made by mixing ethynylestradiol and NESTORONE™ with a stannous octoate-catalyzed polydimethylsiloxane (R-2602 manufactured by NuSil Silicone Technology of Carpinteria, Calif.). The cores contained 12% of ethynylestradiol and 40% NESTORONE™. The cores were 3 mm in diameter and 15 mm or 20 mm in length. The channels in the rings were partially filled with polydimethylsiloxane medical adhesive and the cores were inserted 17 hrs before beginning in vitro measurements. The release patterns are illustrated in FIGS. 9 and 10. The data show that there is no initial burst of ethynylestradiol or NESTORONE™ when core placement is 17 hours prior to release rate measurement. The results also illustrate the effect of core length on release rate.

EXAMPLE 4

Figure 11:
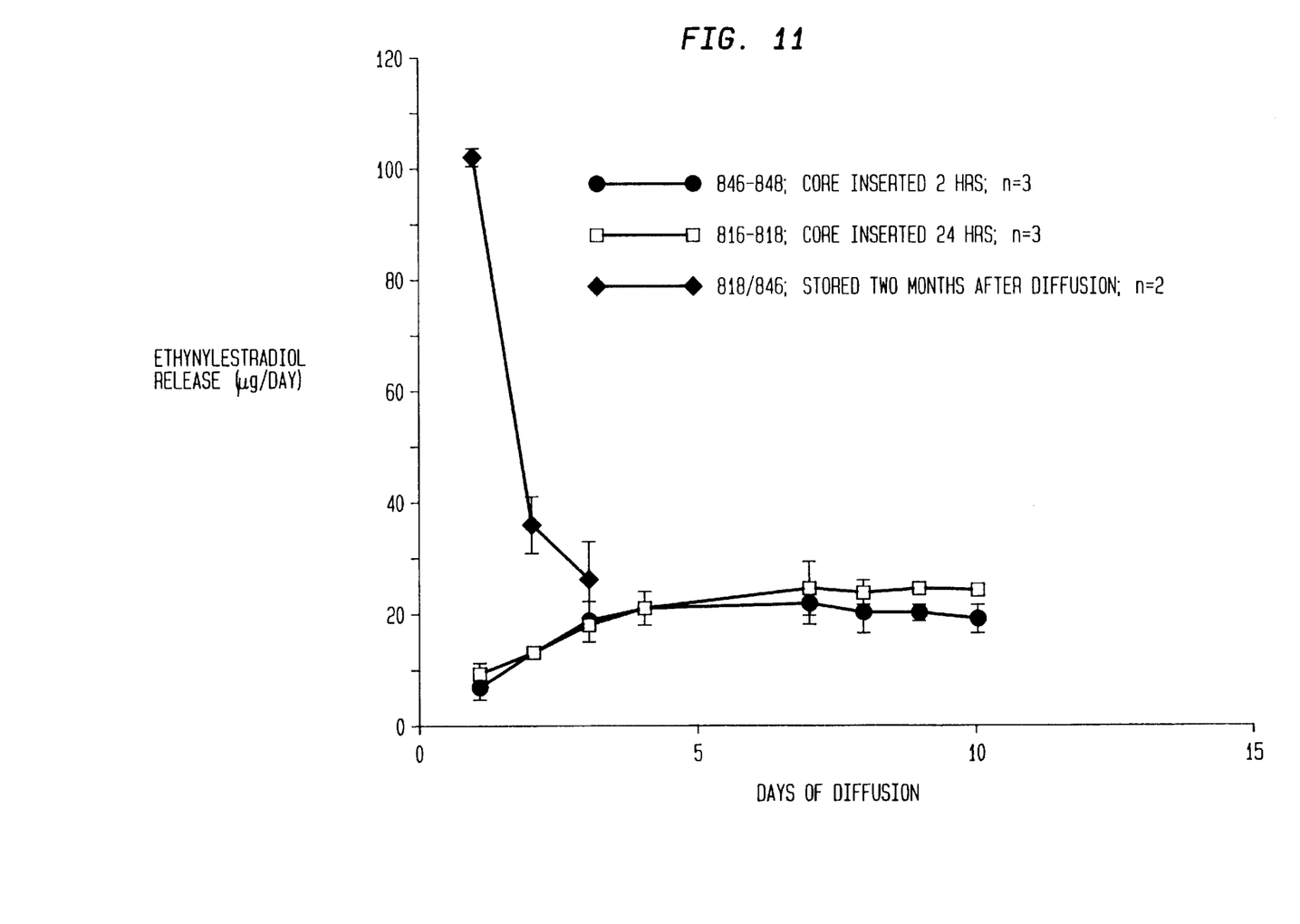
FIG. 11 graphically illustrates the effect of storage time on the magnitude of the initial ethynylestradiol release from vaginal rings of the present invention.

Ring bodies were of the same dimension, composition, and method of manufacture as in Example 3. Cores were of 20 mm length, 3 mm diameter and were made by mixing steroid with a stannous octoate-catalyzed polydimethylsiloxane (MED-6382, manufactured by NuSil Silicone Technology of Carpinteria, Calif.). The cores in rings designated 818 and 848 contained 12% ethynylestradiol. Those in rings designated 846, 847, 816 and 817 contained 12% ethynylestradiol and 40% NESTORON™. The cores were placed either 3 hours or 24 hours before in vitro measurements of release. One ring from each group (818 and 846) was stored for two months at room temperature after the initial 10 days of in vitro release before initial release rate was again measured. The results are shown graphically in FIG. 11. They illustrate the pattern of ethynylestradiol release after short periods between inserting cores and measuring release and the build-up of a potential burst of release on two months storage at room temperature.

EXAMPLE 5

Figure 12:
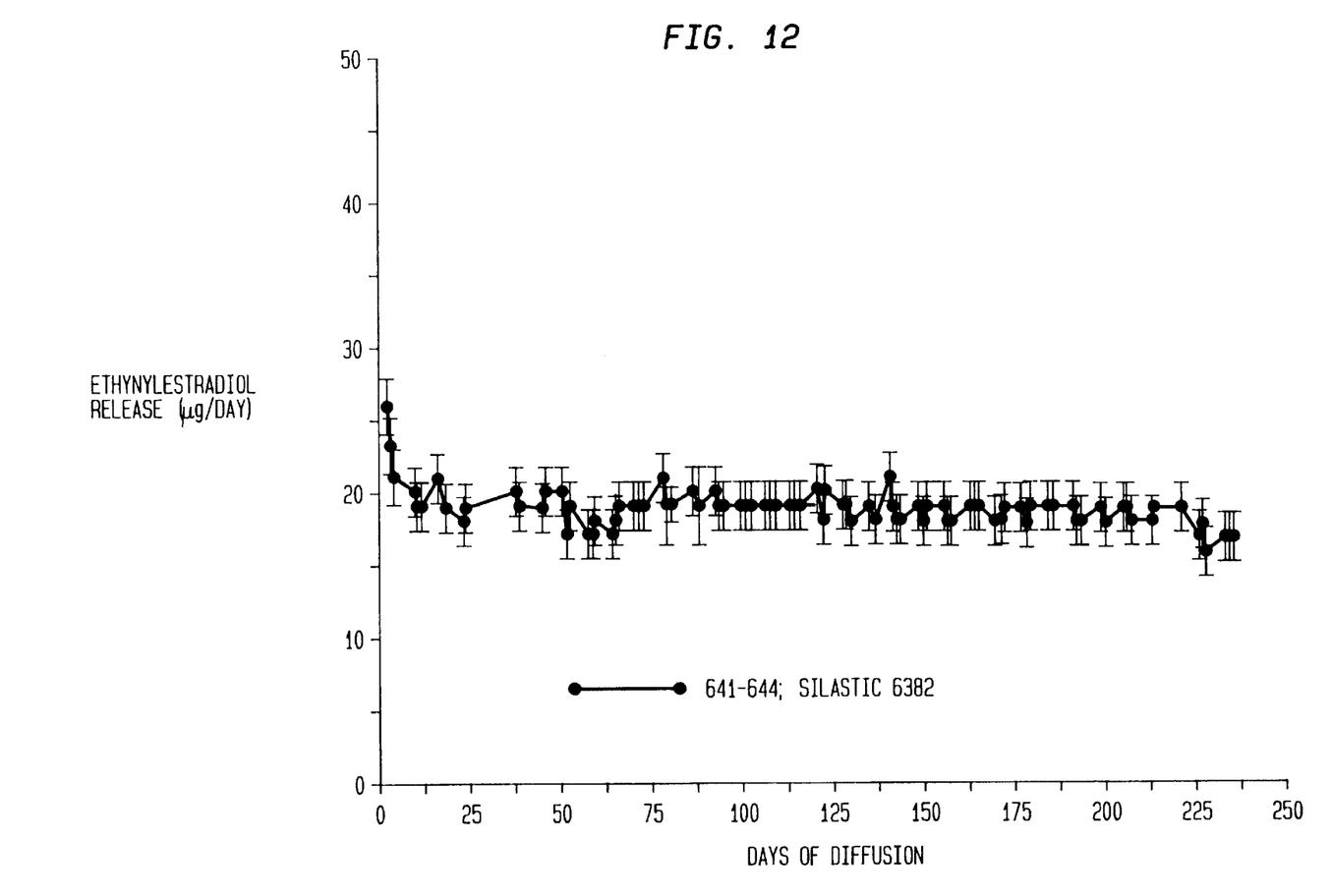
FIGS. 12 and 13 graphically illustrate the release of ethynylestradiol and NESTORONE™ from the same core, and ethynylestradiol only, respectively, from vaginal rings of the present invention assembled 6 days prior to initiating release rate measurements.
Figure 13:
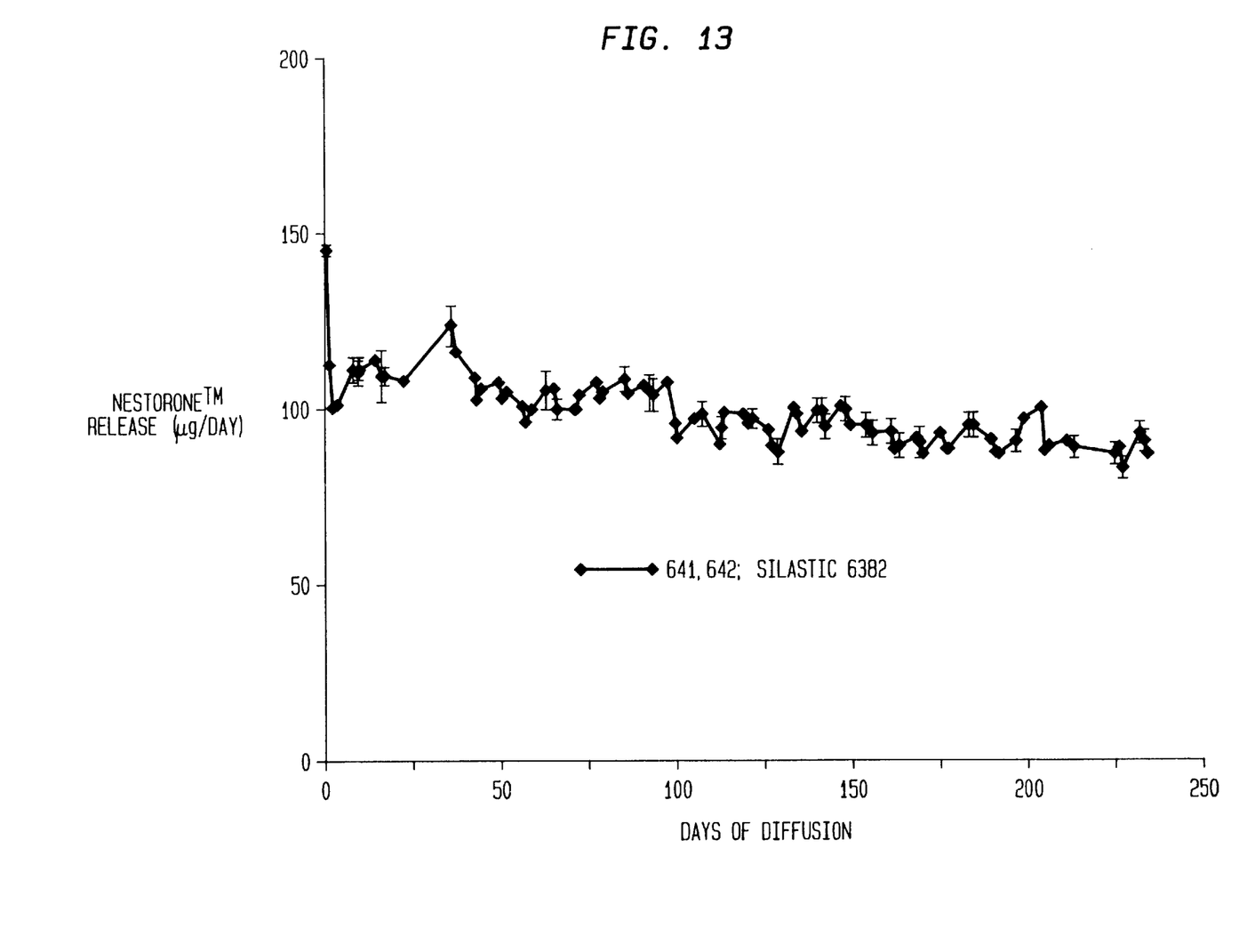

Ring bodies of 8.4 mm cross sectional diameter and 56 mm over all were made with MED-6382. stannous octate-catalyzed polydimethylsiloxane. The ring bodies were formed in a mold containing removable rods to establish channels for core insertion. Cores were of 3×20 mm dimensions. The cores in rings designated 641 and 642 contained both ethynylestradiol and NESTORON™; those for the cores in rings designated 643 and 644 contained only ethynylestradiol. Steroid concentrations in the cores were 12% for ethynylestradiol and 40% for NESTORONE. The elastomer used in all of the cores was MED 6382. The cores were inserted into the ring bodies six days before release rate measurements were initiated. Results are shown in FIGS. 12 and 13. They show a small burst followed by a nearly constant release rate over the eight months in which measurements were made.

The small standard deviations within groups that contained both rings with ethynylestradiol cores and rings with cores containing both steroids illustrate that the presence of NESTORONE™ did not have a significant effect on ethynylestradiol release.

EXAMPLE 6

Ring bodies were made using elastomer LSR 25:10, by molding the elastomer around metal rods. Removal of the metal rods, produced two channels, each having a diameter of 2.8 mm. Cores having a diameter of 3.0 mm, and containing either 12% by weight of ethynylestradiol and 40% by weight of NESTORONE™, or 50% NESTORON™ only, were prepared by injection molding, using silicone elastomer R-2602. After mixing the R-2602 and steroid, four drops of stannous octoate catalyst were reacted with each 6 g mix of steroid/elastomer, which was then injected into the mold. Cores containing both steroids were cut into 18 mm lengths, and those containing NESTORONE™ only were cut into 20 mm lengths. One channel of each ring body was loaded with a core of the NESTORONE™ only, and the second channel was loaded with a core of the combination type, each by inserting the core into the channel using a trocar, and then sealing the open end of the channel by applying a medical adhesive. The in vitro release pattern of the assembled vaginal rings was comparable to the released rate of similar rings, containing cores having diameters slightly smaller than that of the corresponding channels, and wherein adhesive was applied to the channels before and after insertion of the cores. (Data not shown.)

EXAMPLE 7

Figure 14:
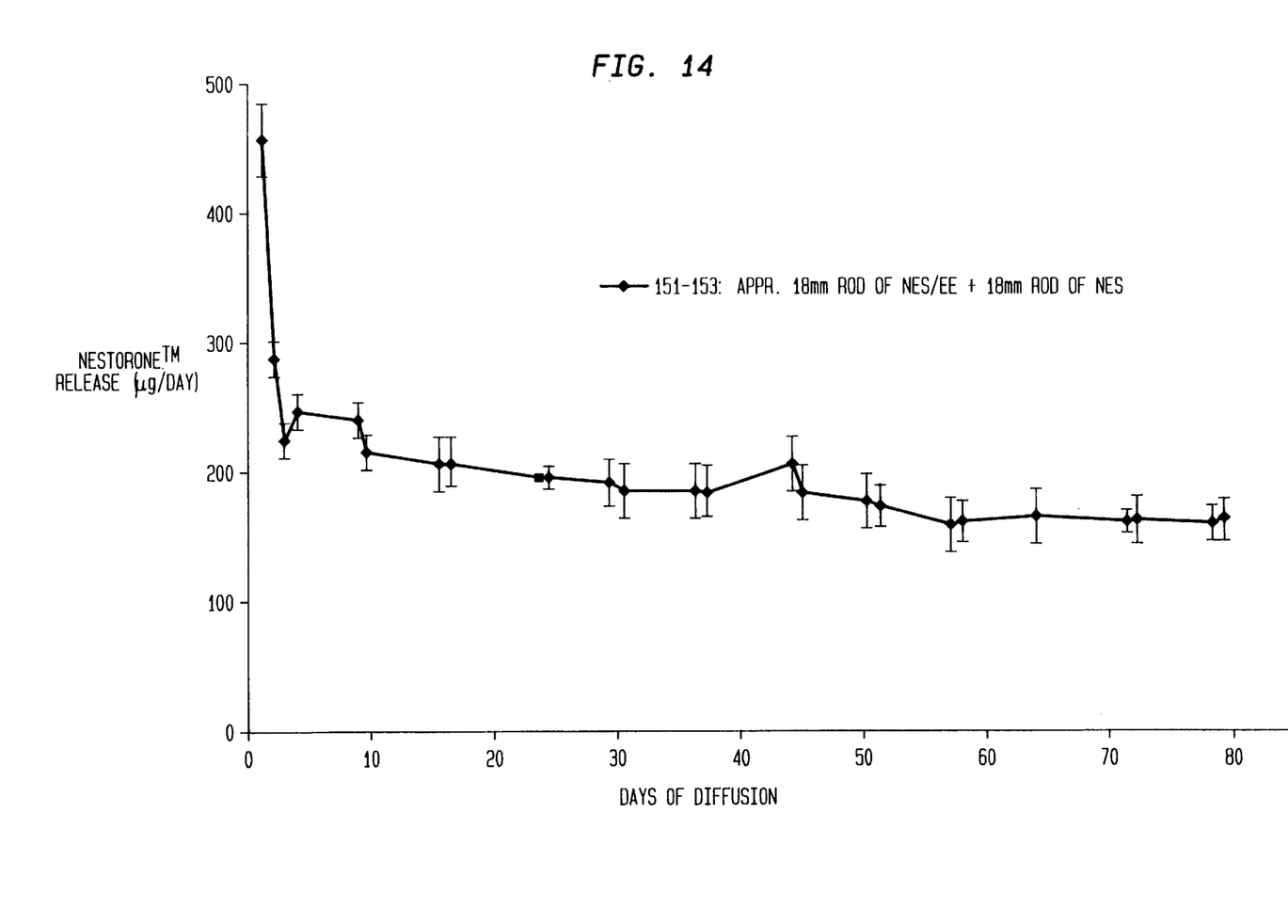
FIGS. 14 and 15 graphically illustrate the release of ethynylestradiol and NESTORONE™ from the same core, and NESTORONE™ only, respectively, from vaginal rings of the present invention.
Figure 15:
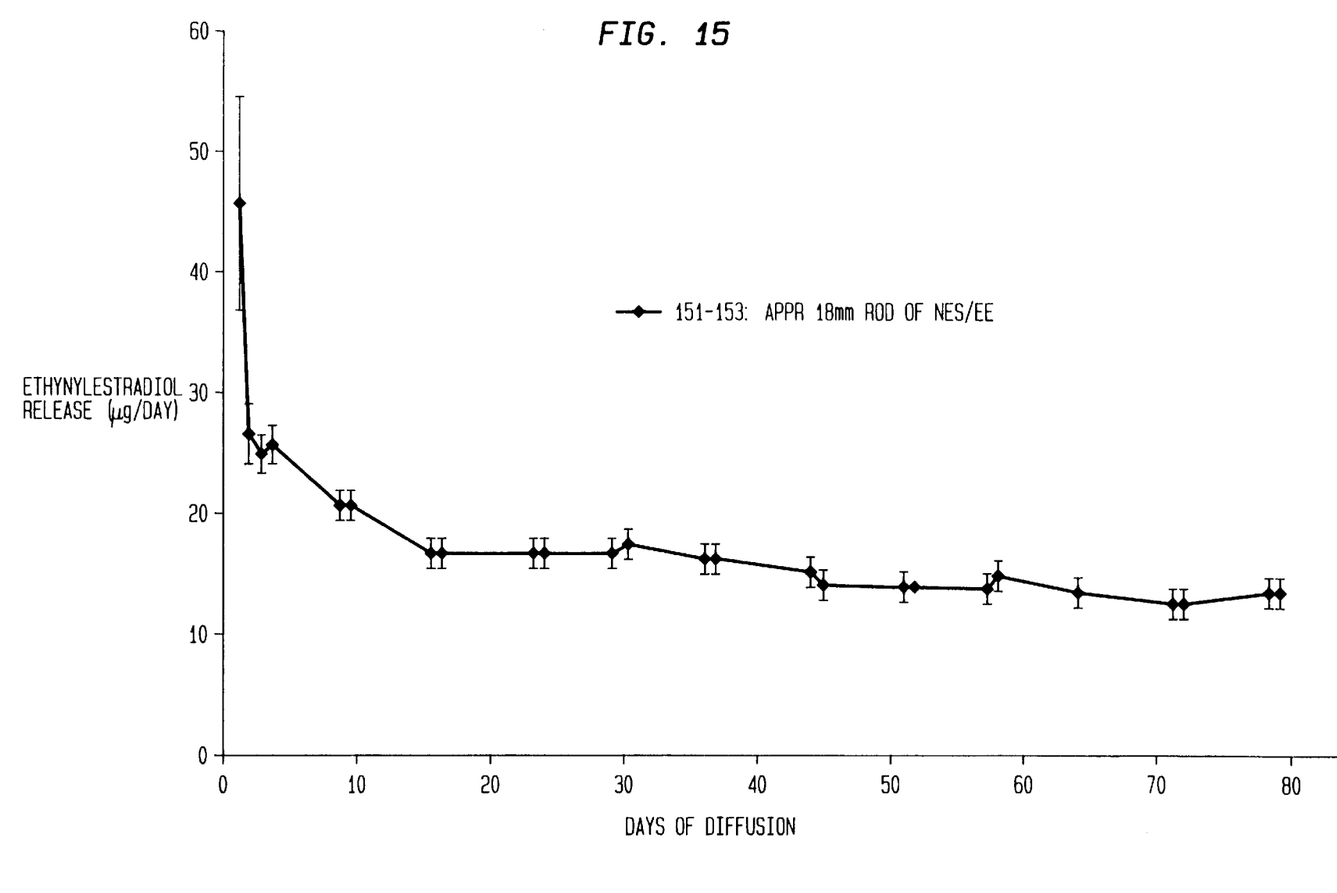

Ring bodies were made from Applied Silicone elastomer LSR 25:10 by injection molding at 120 C. for 3 minutes. Removal of the two metallic rods produced two channels (about 3.8 mm in diameter) in each ring. One channel of each of three rings was filled with a paste composed of Nusil elastomer R-2602 containing 50% NESTORONE™ and 0.5% stannous octoate as the curing agent. The second channel of each of the three rings was filled with a paste composed of Nusil elastomer R-2602 containing 40% NESTORONE™, 14% ethinylestradiol (EE) and 0.5% stannous octoate as the curing agent. The length of paste in each channel was about 18 mm. After paste was injected, the opening of the channel was sealed with MED-1137 silicone adhesive. FIGS. 14 and 15 show the in vitro release of NESTORONE™ and EE, respectively, from these rings. The pattern is one of an initial burst lasting one or two days, followed by a nearly constant release.

All publications cited in the specification are indicative of the level of skill of those skilled in the art to which this invention pertains. All these publications are herein incorporated by reference to the same extent as if each individual publication were specifically and individually indicated to be incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

We claim:

1. A vaginal ring body for making a vaginal ring, comprising a suitably shaped, inert, polymeric material having at least one hollow internal channel defining an opening to the exterior of said body and which channel is adapted to receive an intravaginally administerable drug-containing core through said opening; such that upon assembly of said vaginal ring by positioning said drug-containing core into said hollow internal channel and sealing said channel, no portion of said drug-containing core is exposed to said exterior of said ring body.

2. A kit, comprising:

a vaginal ring body comprising a first polymeric material having at least one hollow internal channel defining an opening to the exterior of said body and which channel is adapted to receive an intravaginally administerable drug-containing core through said opening; and at least one drug-containing core to be positioned in said hollow channel, said drug-containing core comprising a pharmaceutically effective amount of an intravaginally administerable drug dispersed in a second polymeric material, wherein said first and second polymeric materials may be the same or different; such that upon assembly of said vaginal ring by positioning said drug-containing core into said hollow internal channel and sealing said channel, no portion of said drug-containing core is exposed to said exterior of said ring body.

3. The kit of claim 2; further comprising a sealant.

4. A method of administering a drug to a female over a predetermined time period, comprising the steps of;

providing a vaginal ring body comprising a first polymeric material having at least one hollow internal channel defining an opening to the exterior of said body and which channel is adapted to receive a drug-containing core through said opening;

providing a drug-containing core comprising a pharmaceutically effective amount of an intravaginally administerable drug dispersed in a second polymeric material, wherein said first and second polymeric materials may be the same or different;

positioning said drug-containing core in said channel to thereby assemble a vaginal ring suitably prior to use of the vaginal ring; and sealing said channel such that there is no portion of said drug-containing core which is exposed to said exterior of said vaginal ring body.

* * * * *

UNITED STATES PATENT AND TRADEMARK OFFICE
CERTIFICATE OF CORRECTION

PATENT NO. : 6,126,958
DATED : October 3, 2000
INVENTOR(S) : Saleh et al.

It is certified that error appears in the above-identified patent and that said Letters Patent is hereby corrected as shown below:

Column 3, line 26, "a" should read --an--.
Column 6, line 14, "term # internal #" should read --term "internal"--.
Column 6, line 22, "phase # suitably" should read --phase "suitably--.
Column 6, line 23, "use, #" should read --use,"--.
Column 7, line 20, "replasteroidsherapy" should read --replacement therapy--.
Column 7, line 54, "NESTORON" should read --NESTORONE--.
Column 8, line 39, "mechanized, of course" should read --mechanized. Of course--.
Column 9, line 43, "may-be" should read --may be--.
Column 9, line 49, "well suited" should read --well-suited--.
Column 11, line 45, "NESTORON" should read --NESTORONE--.
Column 11, line 58, "cross sectional" should read --cross-sectional--.
Column 11, line 59, "over all" should read --over-all--.
Column 11, line 63, "NESTORON" should read --NESTORONE--.
Column 11, line 66, after "NESTORONE" insert --™--.
Column 12, line 19, "NESTORON" should read --NESTORONE--.

Signed and Sealed this

Fifteenth Day of May, 2001

*Attest:*

NICHOLAS P. GODICI

*Attesting Officer*     *Acting Director of the United States Patent and Trademark Office*